United States Patent
Fukushima et al.

(10) Patent No.: US 7,304,166 B2
(45) Date of Patent: Dec. 4, 2007

(54) BENZENESULFONATE SALT OF 4-FLUORO-2-CYANOPYRROLIDINE DERIVATIVES

(75) Inventors: Hiroshi Fukushima, Tokyo (JP); Akira Hiratate, Tokyo (JP); Masato Takahashi, Tokyo (JP); Kazuya Kameo, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 109 days.

(21) Appl. No.: 10/525,748

(22) PCT Filed: Aug. 27, 2003

(86) PCT No.: PCT/JP03/10828

§ 371 (c)(1),
(2), (4) Date: Oct. 11, 2005

(87) PCT Pub. No.: WO2004/020407

PCT Pub. Date: Mar. 11, 2004

(65) Prior Publication Data

US 2006/0106087 A1 May 18, 2006

(30) Foreign Application Priority Data

Aug. 29, 2002 (JP) .............................. 2002-249821

(51) Int. Cl.
*C07D 207/10* (2006.01)
(52) U.S. Cl. ..................................... 548/540
(58) Field of Classification Search ................. 548/540
See application file for complete search history.

(56) References Cited

U.S. PATENT DOCUMENTS 6,011,155 A * 1/2000 Villhauer .................... 544/333
2004/0072892 A1* 4/2004 Fukushima et al. ......... 514/423

FOREIGN PATENT DOCUMENTS

| EP | 0 092 968 A1 | 11/1983 |
| EP | 0 949 260 A1 | 10/1999 |
| EP | 1 333 025 A1 | 8/2003 |
| EP | 1333025 A1 * | 8/2003 |
| GB | 2 188 630 A | 10/1987 |
| JP | 58-201792 A | 11/1983 |
| JP | 62-240660 A | 10/1987 |
| JP | 2000-198784 A | 7/2000 |
| JP | 2002-531459 A | 9/2002 |
| WO | WO 9819998 A2 * | 5/1998 |
| WO | WO 00/32607 A1 | 6/2000 |
| WO | WO 02/38541 A | 5/2002 |
| WO | WO 0238541 A1 * | 5/2002 |

OTHER PUBLICATIONS

Berge, et al., Journal of Pharmaceutical Sciences, vol. 66 (1), pp. 1-19 (1977).*

* cited by examiner

*Primary Examiner*—Kamal A. Saeed
*Assistant Examiner*—Karen Cheng
(74) *Attorney, Agent, or Firm*—Sughrue Mion, PLLC

(57) ABSTRACT

A benzenesulfonate salt of (2S,4S)-2-cyano-4-fluoro-1-[(2-hydroxy-1,1-dimethyl)ethylamino]acetylpyrrolidine that has an excellent DPPIV inhibition activity as well as physical properties (e.g., stability) required for pharmaceutical preparations. The present invention allows easy obtaining of the compound in high-purity uniform crystal form with excellent solid-state stability.

1 Claim, No Drawings

BENZENESULFONATE SALT OF 4-FLUORO-2-CYANOPYRROLIDINE DERIVATIVES

This is a National Stage of Application No. PCT/JP03/10828 filed Aug. 27, 2003.

TECHNICAL FIELD

The present invention relates to benzenesulfonate salts of 4-fluoro-2-cyanopyrrolidine derivatives.

BACKGROUND ART

Dipeptidyl peptidase IV (DPPIV), a member of serine protease, is widely distributed in tissues (e.g., kidney, liver) and plasma and is involved in the metabolism of various physiologically active peptides.

A compound known as a DPPIV inhibitor is (2S,4S)-2-cyano-4-fluoro-1-[(2-hydroxy-1,1-dimethyl)ethylamino]-acetylpyrrolidine (WO02/38541). However, this compound has low solid-state stability in free form, and its salts with mineral or organic acids disclosed in the application are also disadvantageous in terms of low solid-state stability, low stability under humidified conditions and difficulties in their synthesis, etc.

The present invention aims to provide 4-fluoro-2-cyanopyrrolidine derivatives that have an excellent DPPIV inhibition activity as well as physical properties (e.g., stability) required for pharmaceutical preparations.

DISCLOSURE OF THE INVENTION

To achieve the object stated above, the inventors of the present invention have conducted various studies on 4-fluoro-2-cyanopyrrolidine derivatives and thus have found that preferred stable compounds can be obtained when the derivatives are converted into salt form with benzenesulfonic acid. This finding led to the completion of the present invention.

Namely, the present invention is directed to a benzenesulfonate salt of (2S,4S)-2-cyano-4-fluoro-1-[(2-hydroxy-1,1-dimethyl)ethylamino]acetylpyrrolidine represented by Formula [I]:

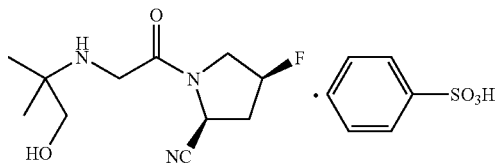

BEST MODE FOR CARRYING OUT THE INVENTION

The benzenesulfonate salt of the present invention may be prepared as follows: (2S,4S)-2-cyano-4-fluoro-1-[(2-hydroxy-1,1-dimethyl)ethylamino]acetylpyrrolidine obtained as described in WO02/38541 is dissolved in an appropriate solvent and mixed with benzenesulfonic acid or a hydrate thereof, either directly or in dissolved form, followed by filtration to collect the resulting precipitate as a target product after addition of a poor solvent, if necessary. When using the above procedure, the compound of the present invention can be readily obtained in uniform crystal form with excellent crystallinity, as compared to other salt compounds (e.g., tosylate salt). It was also possible to produce more stable compositions in terms of stability when mixed with formulation ingredients commonly used for formulating pharmaceutical preparations.

The compound of the present invention can inhibit dipeptidyl peptidase IV in vivo, thus enhancing insulin activity and improving glucose metabolism. The compound of the present invention can also contribute to inhibition of neuropeptide Y metabolism, inhibition of T cell activation, inhibition of cancer cell adhesion to the endothelium, and prevention of HIV virus entry into lymphocytes.

Accordingly, the present invention provides such a pharmaceutical preparation for preventing or treating diseases or conditions capable of being ameliorated by inhibition of dipeptidyl peptidase IV, as exemplified by diabetes mellitus (especially type II), immune diseases, arthritis, obesity, osteoporosis, conditions of impaired glucose tolerance, benign prostatic hyperplasia and skin diseases.

Examples of pharmaceutical preparations for immune diseases include immunosuppressive agents for use in tissue transplantation, for example, cytokine release inhibitors for various autoimmune diseases such as inflammatory enteritis, multiple sclerosis and chronic rheumatoid arthritis (RA), as well as agents useful for preventing or treating AIDS by blocking HIV entry into T-cells and agents for preventing metastasis, especially metastasis of breast and prostate tumors to the lung.

The pharmaceutical preparation of the present invention can be administered systemically or topically via oral route or parenteral (e.g., intrarectal, subcutaneous, intramuscular, intravenous, percutaneous) routes.

For use as a pharmaceutical preparation, the compound of the present invention may be formulated into any desired dosage form selected from solid compositions, liquid compositions and other compositions, as appropriate for the intended purpose. The pharmaceutical preparation of the present invention can be prepared by blending the compound of the present invention with pharmaceutically acceptable carrier(s). More specifically, the compound of the present invention may be supplemented with commonly used excipients, extenders, binders, disintegrating agents, coating agents, sugar-coating agents, pH adjustors, solubilizers, aqueous or non-aqueous solvents and so on, and then formulated using standard techniques into tablets, pills, capsules, granules, powders, solutions, emulsions, suspensions, injections, etc.

Also, the compound of the present invention may be modified to form an inclusion compound with, e.g., α-, β- or γ-cyclodextrin or methylated cyclodextrin before being formulated.

The dose of the compound of the present invention will vary depending on the disease or symptom to be treated, body weight, age, sex, the route of administration, etc. The adult dose for oral administration is preferably about 1 to about 1000 mg/person/day, more preferably about 10 to about 200 mg/person/day, given as a single dose or in divided doses per day.

The present invention will be further illustrated in the following reference examples, example and test examples.

REFERENCE EXAMPLE 1

Synthesis of (2S,4S)-2-cyano-4-fluoro-1-[(2-hydroxy-1,1-dimethyl)ethylamino]acetylpyrrolidine hydrochloride salt To a suspension of (2S,4S)-2-cyano-4-fluoro-1-[(2-hydroxy-1,1-dimethyl)ethylamino]acetylpyrrolidine (5.00 g)

in methanol (75 mL), 4M hydrochloric acid (in ethyl acetate, 6.17 mL) was added to give a clear solution. To this solution, diisopropyl ether (300 mL) was added and stirred, followed by filtration to collect the precipitated powders, which were the titled compound (5.47 g) as a colorless powder.

Melting point: 197-198° C.

REFERENCE EXAMPLE 2

Synthesis of (2S,4S)-2-cyano-4-fluoro-1-[(2-hydroxy-1,1-dimethyl)ethylamino]acetylpyrrolidine methanesulfonate salt To a suspension of (2S,4S)-2-cyano-4-fluoro-1-[(2-hydroxy-1,1-dimethyl)ethylamino]acetylpyrrolidine (0.15 g) in methanol (0.92 mL), a solution of methanesulfonic acid (0.042 mL) in methanol (0.08 mL) was added to give a clear solution. This solution was added dropwise to diisopropyl ether (5 mL) while stirring. The precipitated powders were collected by filtration to give the titled compound (0.20 g) as a colorless powder.

Melting point: 179-180° C.

EXAMPLE 1

Synthesis of (2S,4S)-2-cyano-4-fluoro-1-[(2-hydroxy-1,1-dimethyl)ethylamino]acetylpyrrolidine benzenesulfonate salt (1) (2S,4S)-2-Cyano-4-fluoro-1-[(2-hydroxy-1,1-dimethyl)-ethylamino]acetylpyrrolidine 2-Amino-2-methyl-1-propanol (0.54 g) was dissolved in a mixed solvent of tetrahydrofuran (7.5 mL) and ethanol (2.5 ml). To this solution, (2S,4S)-1-bromoacetyl-2-cyano-4-fluoropyrrolidine (0.71 g) was added under ice cooling and then stirred at room temperature for 1 hour. The precipitated crystals were collected by filtration to give the titled compound (0.36 g) as a colorless solid. Further, the filtrate was also purified by silica gel column chromatography (developing solvent; chloroform:methanol:25% aqueous ammonia=300:10:1) to give the titled compound (0.22 g).

(2) (2S,4S)-2-Cyano-4-fluoro-1-[(2-hydroxy-1,1-dimethyl)-ethylamino]acetylpyrrolidine benzenesulfonate salt (2S,4S)-2-Cyano-4-fluoro-1-[(2-hydroxy-1,1-dimethyl) ethylamino]acetylpyrrolidine (20 g) was dissolved under heating in methanol (300 mL). Powders were precipitated from this solution upon addition of a solution of benzenesulfonic acid monohydrate (15.2 g) in methanol (30 mL). After addition of diisopropyl ether (330 mL) to this suspension, the powders were collected by filtration to give the titled compound (31.5 g) as a colorless powder.

Melting point: 220-221° C.

TEST EXAMPLE 1

Testing for Weight Change Under Humidified Conditions

Each analyte (10.0 mg) was metered into a microtube (diameter: 8 mm, length: 50 mm) and allowed to stand in a desiccator containing water in such a manner as to keep the tube from coming into contact with water. The desiccator was allowed to stand at room temperature. The analytes were monitored for their state and measured for their weight with time. Changes in weight were expressed as percentages (%).

<Changes in Weight and State>

TABLE 1

|  | Day 1 | Day 2 | Day 3 |
| --- | --- | --- | --- |
| Compound of Reference Example 1 | +44% Deliquescence | — | — |
| Compound of Reference Example 2 | +28% | +71% Deliquescence | — |
| Compound of Example 1 | ±0% | ±0% | ±0% No change in appearance |

The hydrochloride salt of Reference Example 1 and the methanesulfonate salt of Reference Example 2 both absorbed moisture and thus deliquesced, whereas the benzenesulfonate salt of Example 1 showed no change in weight and no deliquescence.

TEST EXAMPLE 2

Solid-State Stability Testing

Each analyte (about 1 mg) was precisely metered and stored in a screw-capped test tube covered with aluminum foil for light shielding, which was sealed under heated conditions (70° C.) or opened under heated and humidified conditions (40° C., 75% RH). The remaining percentage of each drug was measured in the following manner. After completion of a given period of storage, the test tubes were supplemented with 10 ml HPLC mobile phase to dissolve the analytes and then provided for quantification by HPLC. The results were compared in area with the initial values obtained before heating or before heating and humidification to calculate the remaining percentage of drugs.

*HPLC Conditions

Column: CAPCELL PAK UG120, 5 μm, φ4.6×150 mm (SHISEIDO)

Column temperature: 40° C.

Detection: UV absorptiometer (Detection wavelength: 210 nm)

Flow rate: 1.0 ml/min

Injection volume: 10 μl

Mobile phase: water/acetonitrile/phosphoric acid/SDS (700:300:1:2)

<Remaining Percentage of Drugs>

TABLE 2

|  | 70° C. for 3 days | 40° C., 75% for 1 month |
| --- | --- | --- |
| Compound of Reference Example 1 | 97.0% | 92.6% |
| Compound of Reference Example 2 | 95.5% | 95.9% |
| Compound of Example 1 | 99.3% | 99.6% |

The hydrochloride salt of Reference Example 1 and the methanesulfonate salt of Reference Example 2 showed a remaining percentage of 97% or less under either condition, whereas the benzenesulfonate salt of Example 1 showed a remaining percentage of 99% or more under either condition.

TEST EXAMPLE 3

Compatibility Testing with Additives

This testing was performed according to the report of Serajuddin A. T. M. et al. (J. Pharm. Sci., 88, 696-704, 1999). A drug substance and additives were metered into a screw-capped test tube according to Recipe A (10 mg drug substance, 68 mg crystalline cellulose, 2 mg magnesium stearate) or Recipe B (10 mg drug substance, 68 mg lactose, 2 mg hydrogenated oil) and mixed in a rotary mixer (MIX-ROTAR VMR-5, Iuchi Seieido Co., Ltd., Japan) for 1 hour. The mixture according to Recipe A or B was further stirred using a vortex mixer (TOUCH MIXER MT-31, Yamato Scientific Co., Ltd., Japan), provided that Recipe A was supplemented with no additional ingredient, while Recipe B was supplemented with 16 µl purified water. The mixtures were stored at 65° C. for 1 week under sealed and completely light-shielded conditions and then measured for drug content after storage to calculate the remaining percentage of each drug in each recipe.

The drug content was determined in the following manner. The stored samples were supplemented with 10 ml of 50% methanol, ultrasonicated for 30 minutes (using a BRANSONIC 5200, BRANSON Co.) to disperse and extract the drugs, and then shaken in a shaker for 1 hour. The resulting solutions were transferred to 50 ml measuring flasks and the solutions remaining in the test tubes were also collected by washing with 50% methanol, followed by filling up to 50 ml with 50% methanol. The flasks were further ultrasonicated for 30 minutes. The resulting solutions were each filtered through a 0.45 µm membrane filter, 5 ml of which was sampled and filled up with 50% methanol in a 10 ml measuring flask for use as a sample solution and then quantified by HPLC. HPLC conditions were the same as used in Test Example 2.

| <Remaining percentage of drugs> | | |
| --- | --- | --- |
| | Recipe A | Recipe B |
| Compound of Reference Example 2 | 91.6% | 74.5% |
| Compound of Example 1 | 99.1% | 91.6% |

In the case of Recipe A, the remaining percentage of drug was reduced to 91.6% in the methanesulfonate salt of Reference Example 2, whereas there was almost no reduction in the remaining percentage of the benzenesulfonate salt of Example 1. Likewise, even in the case of Recipe B where the methanesulfonate salt showed a remaining percentage reduced to 74.5%, the benzenesulfonate salt maintained a remaining percentage of 90% or more.

The compound of Example 1 was confirmed to resist deterioration even when supplemented with formulation ingredients used for formulating pharmaceutical preparations, thus enabling the provision of formulated compositions stable enough as pharmaceutical preparations.

INDUSTRIAL APPLICABILITY

The compound of the present invention can be readily obtained in high-purity uniform crystal form with excellent stability under highly humidified conditions. This fact eliminates risks such as powder adhesion onto machines and reduced flowability during preparation, and enables a stable supply of pharmaceutical preparations containing the compound. Because of its excellent solid-state stability, the compound of the present invention is also free from problems such as changes in appearance and transformation of crystal structure, has resistance to extreme conditions required for formulating pharmaceutical preparations, and also ensures long-term quality maintenance even when supplemented with formulation ingredients.

The invention claimed is:

1. A benzenesulfonate salt of (2S,4S)-2-cyano-4-fluoro-1-[(2-hydroxy-1,1-dimethyl)ethylamino]acetylpyrrolidine.

* * * * *